United States Patent [19]

King et al.

[11] 4,263,152

[45] Apr. 21, 1981

[54] PROCESS OF PREPARING MOLYBDENUM COMPLEXES, THE COMPLEXES SO-PRODUCED AND LUBRICANTS CONTAINING SAME

[75] Inventors: John M. King, San Rafael; Louis deVries, Greenbrae, both of Calif.

[73] Assignee: Chevron Research Company, San Francisco, Calif.

[21] Appl. No.: 52,696

[22] Filed: Jun. 28, 1979

[51] Int. Cl.$^3$ .............................................. C10M 1/54
[52] U.S. Cl. ................................. 252/46.4; 252/34.7; 252/46.7; 252/49.7; 252/400 R; 252/400 A; 260/125; 260/128; 260/137
[58] Field of Search .................. 252/34.7, 46.4, 49.7, 252/51, 25, 400 R, 400 A; 260/125, 128, 137

[56] References Cited

U.S. PATENT DOCUMENTS

| | | | |
|---|---|---|---|
| 3,140,997 | 7/1964 | Price | 252/25 X |
| 3,223,625 | 12/1965 | Cyphers et al. | 252/49.7 X |
| 3,281,355 | 10/1966 | Cyphers et al. | 252/25 X |
| 3,290,245 | 12/1966 | Elliott et al. | 252/49.7 X |
| 3,509,051 | 4/1970 | Farmer et al. | 252/46.4 X |
| 3,591,496 | 7/1971 | Vickars et al. | 252/25 X |
| 4,098,705 | 7/1978 | Sakurai et al. | 252/33.6 |
| 4,164,473 | 8/1979 | Coupland et al. | 252/42.7 X |
| 4,192,757 | 3/1980 | Brewster | 252/42.7 X |

FOREIGN PATENT DOCUMENTS

| | | | |
|---|---|---|---|
| 1076298 | 2/1960 | Fed. Rep. of Germany | 252/46.4 |
| 1095973 | 12/1960 | Fed. Rep. of Germany | 252/34.7 |
| 1085903 | 10/1967 | United Kingdom . | |
| 2037317 | 7/1980 | United Kingdom . | |

*Primary Examiner*—Andrew Metz
*Attorney, Agent, or Firm*—D. A. Newell; S. R. LaPaglia; V. J. Cavalieri

[57] ABSTRACT

Antioxidant additives for lubricating oil are prepared by combining water, an acidic molybdenum compound, a basic nitrogen compound complex and a sulfur source to form a sulfur- and molybdenum-containing composition.

17 Claims, No Drawings

PROCESS OF PREPARING MOLYBDENUM COMPLEXES, THE COMPLEXES SO-PRODUCED AND LUBRICANTS CONTAINING SAME

FIELD OF THE INVENTION

This invention relates to new lubricating oil compositions. More specifically, it relates to new lubricating oil compositions containing antioxidant molybdenum compounds.

BACKGROUND OF THE INVENTION

Molybdenum disulfide has long been known as a desirable additive for use in lubricating oil compositions. However, one of its major detriments is its lack of oil solubility. Molybdenum disulfide is ordinarily finely ground and then dispersed in the lubricating oil composition to impart friction modifying and antiwear properties. Finely ground molybdenum disulfide is not an effective oxidation inhibitor in lubricating oils.

As an alternative to finely grinding the molybdenum disulfide, a number of different approaches involving preparing salts of molybdenum compounds have been tried. One type of compound which has been prepared is molybdenum dithiocarbamates. Representative compositions are described in U.S. Pat. No. 3,419,589, which teaches molybdenum (VI) dioxide dialkyldithiocarbamates; U.S. Pat. No. 3,509,051, which teaches sulfurized oxymolybdenum dithiocarbamates; and U.S. Pat. No. 4,098,705, which teaches sulfur containing molybdenum dihydrocarbyl dithiocarbamate compositions.

An alternative approach is to form dithiophosphates instead of dithiocarbamates. Representative of this type of molybdenum compound are the compositions described in U.S. Pat. No. 3,494,866, such as oxymolybdenum diisopropylphosphorodithioate.

U.S. Pat. No. 3,184,410 describes certain dithiomolybdenyl acetylacetonates for use in lubricating oils.

Braithwaite and Greene in *Wear*, 46 (1978) 405–432 describe various molybdenum-containing compositions for use in motor oils.

U.S. Pat. No. 3,349,108 teaches a molybdenum trioxide complex with diethylenetriamine for use as an additive for molten steel.

Russian Pat. No. 533,625 teaches lube oil additives prepared from ammonium molybdate and alkenylated polyamines.

Another way to incorporate molybdenum compounds in oil is to prepare a colloidal complex of molybdenum disulfide or oxysulfides dispersed using known dispersants. U.S. Pat. No. 3,223,625 describes a procedure in which an acidic aqueous solution of certain molybdenum compounds is prepared and then extracted with a hydrocarbon ether dispersed with an oil soluble dispersant and then freed of the ether. U.S. Pat. No. 3,281,355 teaches the preparation of a dispersion of molybdenum disulfide by preparing a mixture of lubricating oil, dispersant, and a molybdenum compound in water or $C_{1-4}$ aliphatic alcohol, contacting this with a sulfide ion generator and then removing the solvent. Dispersants said to be effective in this procedure are petroleum sulfonates, phenates, alkylphenate sulfides, phosphosulfurized olefins and combinations thereof.

SUMMARY OF THE INVENTION

It has now been found that a lubricating oil additive can be prepared by combining an acidic molybdenum compound, a polar promoter, a basic nitrogen-containing composition, and a sulfur source to form a molybdenum and sulfur containing complex.

DETAILED DESCRIPTION OF THE INVENTION

Lubricating oil compositions containing the additive prepared as disclosed herein are effective as either fluid and grease compositions (depending upon the specific additive or additives employed) for inhibiting oxidation, imparting antiwear and extreme pressure properties, and/or modifying the friction properties of the oil which may, when used as a crankcase lubricant, lead to improved mileage.

The precise molecular formula of the molybdenum compositions of this invention is not known with certainty; however, they are believed to be compounds in which molybdenum, whose valences are satisfied with atoms of oxygen or sulfur, is either complexed by or the salt of one or more nitrogen atoms of the basic nitrogen containing composition used in the preparation of these compositions.

The molybdenum compounds used to prepare the compositions of this invention are acidic molybdenum compounds. By acidic is meant that the molybdenum compounds will react with a basic nitrogen compound as measured by ASTM test D-664 or D-2896 titration procedure. Typically these molybdenum compounds are hexavalent and are represented by the following compositions: molybdic acid, ammonium molybdate, sodium molybdate, potassium molybdate and other alkaline metal molybdates and other molybdenum salts such as hydrogen salts, e.g. hydrogen sodium molybdate, $MoOCl_4$, $MoO_2Br_2$, $Mo_2O_3Cl_6$, molybdenum trioxide or similar acidic molybdenum compounds. Preferred acidic molybdenum compounds are molybdic acid, ammonium molybdate, and alkali metal molybdates. Particularly preferred are molybdic acid and ammonium molybdate.

The basic nitrogen compound must have a basic nitrogen content as measured by ASTM D-664 or D-2896. It is preferably oil-soluble. Typical of such compositions are succinimides, carboxylic acid amides, hydrocarbyl monoamines, hydrocarbon polyamines, Mannich bases, phosphonamides, thiophosphonamides, phosphoramides, dispersant viscosity index improvers, and mixtures thereof. These basic nitrogen-containing compounds are described below (keeping in mind the reservation that each must have at least one basic nitrogen). Any of the nitrogen-containing compositions may be after-treated with e.g., boron, using procedures well known in the art so long as the compositions continue to contain basic nitrogen. These after-treatments are particularly applicable to succinimides and Mannich base compositions.

The mono and polysuccinimides that can be used to prepare the lubricating oil additives described herein are disclosed in numerous references and are well known in the art. Certain fundamental types of succinimides and the related materials encompassed by the term of art "succinimide" are taught in U.S. Pat. Nos. 3,219,666, 3,172,892, and 3,272,746, the disclosures of which are hereby incorporated by reference. The term "succinimide" is understood in the art to include many of the amide, imide, and amidine species which are also formed by this reaction. The predominant product however is a succinimide and this term has been generally accepted as meaning the product of a reaction of an alkenyl substituted succinic acid or anhydride with a nitrogen containing compound. Preferred succinimides, because of their commercial availability, are those succinimides prepared from a hydrocarbyl succinic anhydride, wherein the hydrocarbyl group contains from about 24 to about 350 carbon atoms, and an ethylene amine, said ethylene amines being especially characterized by ethylene diamine, diethylene triamine, triethylene tetraamine, and tetraethylene pentaamine. Particularly preferred are those succinimides prepared from polyisobutenyl succinic anhydride of 70 to 128 carbon atoms and tetraethylene pentaamine or triethylene tetraamine or mixtures thereof.

Also included within the term succinimide are the cooligomers of a hydrocarbyl succinic acid or anhydride and a poly secondary amine containing at least one tertiary amino nitrogen in addition to two or more secondary amino groups. Ordinarily this composition has between 1,500 and 50,000 average molecular weight. A typical compound would be that prepared by reacting polyisobutenyl succinic anhydride and ethylene dipiperazine. Compositions of this type are disclosed in U.S. Ser. No. 816,063, filed July 15, 1977 the disclosure of which is hereby incorporated by reference.

Carboxylic amide compositions are also suitable starting materials for preparing the products of this invention. Typical of such compounds are those disclosed in U.S. Pat. No. 3,405,064, the disclosure of which is hereby incorporated by reference. These compositions are ordinarily prepared by reacting a carboxylic acid or anhydride or ester thereof, having at least 12 to about 350 aliphatic carbon atoms in the principal aliphatic chain and, if desired, having sufficient pendant aliphatic groups to render the molecule oil soluble with an amine or a hydrocarbyl polyamine, such as an ethylene amine, to give a mono or polycarboxylic acid amide. Preferred are those amides prepared from (1) a carboxylic acid of the formula $R^2COOH$, where $R^2$ is $C_{12-20}$ alkyl or a mixture of this acid with a polyisobutenyl carboxylic acid in which the polyisobutenyl group contains from 72 to 128 carbon atoms and (2) an ethylene amine, especially triethylene tetraamine or tetraethylene pentaamine or mixtures thereof.

Another class of compounds which are useful in this invention are hydrocarbyl monoamines and hydrocarbyl polyamines, preferably of the type disclosed in U.S. Pat. No. 3,574,576, the disclosure of which is hereby incorporated by reference. The hydrocarbyl, which is preferably alkyl, or olefinic having one or two sites of unsaturation, usually contains from 9 to 350, preferably from 20 to 200 carbon atoms. Particularly preferred hydrocarbyl polyamines are those which are derived, e.g., by reacting polyisobutenyl chloride and a polyalkylene polyamine, such as an ethylene amine, e.g. ethylene diamine, diethylene triamine, tetraethylene pentaamine, 2-aminoethylpiperazine, 1,3-propylene diamine, 1,2-propylenediamine and the like.

Another class of compounds useful for supplying basic nitrogen are the Mannich base compositions. These compositions are prepared from a phenol or $C_{9-200}$ alkylphenol, an aldehyde, such as formaldehyde or formaldehyde precursor such as paraformaldehyde, and an amine compound. The amine may be a mono or polyamine and typical compositions are prepared from an alkylamine, such as methylamine or an ethylene amine, such as, diethylene triamine, or tetraethylene pentaamine and the like. The phenolic material may be sulfurized and preferably is dodecylphenol or a $C_{80-100}$ alkylphenol. Typical Mannich bases which can be used in this invention are disclosed in U.S. Pat. No. 4,157,309 and U.S. Pat. Nos. 3,649,229, 3,368,972 and 3,539,663, the disclosures of which are hereby incorporated by reference. The last application discloses Mannich bases prepared by reacting an alkylphenol having at least 50 carbon atoms, preferably 50 to 200 carbon atoms with formaldehyde and an alkylene polyamine $HN(ANH)_nH$ where A is a saturated divalent alkyl hydrocarbon of 2 to 6 carbon atoms and n is 1-10 and where the condensation product of said alkylene polyamine may be further reacted with urea or thiourea. The utility of these Mannich bases as starting materials for preparing lubricating oil additives can often be significantly improved by treating the Mannich base using conventional techniques to introduce boron into the composition.

Another class of composition useful for preparing the additives of this invention are the phosphoramides and phosphonamides such as those disclosed in U.S. Pat. Nos. 3,909,430 and 3,968,157 the disclosures of which are hereby incorporated by reference. These compositions may be prepared by forming a phosphorus compound having at least one P-N bond. They can be prepared, for example, by reacting phosphorus oxychloride with a hydrocarbyl diol in the presence of a monoamine or by reacting phosphorus oxychloride with a difunctional secondary amine and a mono-functional amine. Thiophosphoramides can be prepared by reacting an unsaturated hydrocarbon compound containing from 2 to 450 or more carbon atoms, such as polyethylene, polyisobutylene, polypropylene, ethylene, 1-hexene, 1,3-hexadiene, isobutylene, 4-methyl-1-pentene, and the like, with phosphorus pentasulfide and nitrogen-containing compound as defined above, particularly an alkylamine, alkyldiamine, alkylpolyamine, or an alkyleneamine, such as ethylene diamine, diethylenetriamine, triethylenetetraamine, tetraethylenepentaamine, and the like.

Another class of nitrogen-containing compositions useful in preparing the molybdenum compositions of this invention includes the so-called dispersant viscosity index improvers (VI improvers). These VI improvers are commonly prepared by functionalizing a hydrocarbon polymer, especially a polymer derived from ethylene and/or propylene, optionally containing additional units derived from one or more co-monomers such as alicyclic or aliphatic olefins or diolefins. The functionalization may be carried out by a variety of processes which introduce a reactive site or sites which usually has at least one oxygen atom on the polymer. The polymer is then contacted with a nitrogen-containing source to introduce nitrogen-containing functional groups on the polymer backbone. Commonly used nitrogen sources include any basic nitrogen compound especially those nitrogen-containing compounds and compositions described herein. Preferred nitrogen sources are alkylene amines, such as ethylene amines, alkyl amines, and Mannich bases.

Preferred basic nitrogen compounds for use in this invention are succinimides, carboxylic acid amides, and Mannich bases.

Representative sulfur sources are sulfur, hydrogen sulfide, sulfur monochloride, sulfur dichloride, phosphorus pentasulfide, $R_2S_x$ where R is hydrocarbyl, preferably $C_{1-40}$ alkyl, and x is at least 2, inorganic sulfides and polysulfides such as $(NH_4)_2S_x$, where x is at least 1, thioacetamide, thiourea, and mercaptans of the formula RSH where R is as defined above. Also useful as sulfurizing agents are traditional sulfur-containing antioxidants such as wax sulfides and polysulfides, sulfurized olefins, sulfurized carboxylic and esters and sulfurized ester-olefins, and sulfurized alkylphenols and the metal salts thereof.

The sulfurized fatty acid esters are prepared by reacting sulfur, sulfur monochloride, and/or sulfur dichloride with an unsaturated fatty ester under elevated temperatures. Typical esters include $C_1-C_{20}$ alkyl esters of $C_8-C_{24}$ unsaturated fatty acids, such as palmitoleic, oleic, ricinoleic, petroselinic, vaccenic, linoleic, linolenic, oleostearic, licanic, paranaric, tariric, gadoleic, arachidonic, cetoleic, etc. Particularly good results have been obtained with mixed unsaturated fatty acid esters, such as are obtained from animal fats and vegetable oils, such as tall oil, linseed oil, olive oil, caster oil, peanut oil, rape oil, fish oil, sperm oil, and so forth.

Exemplary fatty esters include lauryl tallate, methyl oleate, ethyl oleate, lauryl oleate, cetyl oleate, cetyl linoleate, lauryl ricinoleate, oleyl linoleate, oleyl stearate, and alkyl glycerides.

Cross-sulfurized ester olefins, such as a sulfurized mixture of $C_{10}-C_{25}$ olefins with fatty acid esters of $C_{10}-C_{25}$ fatty afids and $C_1-C_{25}$ alkyl or alkenyl alcohols, wherein the fatty acid and/or the alcohol is unsaturated may also be used.

Sulfurized olefins are prepared by the reaction of the $C_3-C_6$ olefin or a low-molecular-weight polyolefin derived therefrom with a sulfur-containing compound such as sulfur, sulfur monochloride, and/or sulfur dichloride.

Also useful are the aromatic and alkyl sulfides, such as dibenzyl sulfide, dixylyl sulfide, dicetyl sulfide, diparaffin wax sulfide and polysulfide, cracked wax-olefin sulfides and so forth. They can be prepared by treating the starting material, e.g., olefinically unsaturated compounds, with sulfur, sulfur monochloride, and sulfur dichloride. Particularly preferred are the paraffin wax thiomers described in U.S. Pat. No. 2,346,156.

Sulfurized alkyl phenols and the metal salts thereof include compositions such as sulfurized dodecylphenol and the calcium salts thereof. The alkyl group ordinarily contains from 9–300 carbon atoms. The metal salt may be preferably, a group I or group II salt, especially sodium, calcium, magnesium, or barium.

Preferred sulfur sources are sulfur, hydrogen sulfide, phosphorus pentasulfide, $R_2S_x$ where R is hydrocarbyl, preferably $C_{1-10}$ alkyl, and x is at least 3, mercaptans wherein R is $C_{1-10}$ alkyl, inorganic sulfides and polysulfides, thioacetamide, and thiourea. Most preferred sulfur sources are sulfur, hydrogen sulfide, phosphorus pentasulfide, and inorganic sulfides and polysulfides.

The polar promoter used in the process of this invention is one which facilitates the interaction between the acidic molybdenum compound and the basic nitrogen compound. A wide variety of such promoters are well known to those skilled in the art. Typical promoters are 1,3-propanediol, 1,4-butane-diol, diethylene glycol, butyl cellosolve, propylene glycol, 1,4-butyleneglycol, methyl carbitol, ethanolamine, diethanolamine, N-methyl-diethanol-amine, dimethyl formamide, N-methyl acetamide, dimethyl acetamide, methanol, ethylene glycol, dimethyl sulfoxide, hexamethyl phosphoramide, tetrahydrofuran and water. Preferred are water and ethylene glycol. Particularly preferred is water.

While ordinarily the polar promoter is separately added to the reaction mixture, it may also be present, particularly in the case of water, as a component of non-anhydrous starting materials or as waters of hydration in the acidic molybdenum compound, such as $(NH_4)_6Mo_7O_{24}.4\ H_2O$. Water may also be added as ammonium hydroxide.

A method for preparing compositions of this invention is to prepare a solution of the acidic molybdenum precursor and a polar promoter with a basic nitrogen-containing compound with or without diluent. The diluent is used, if necessary, to provide a suitable viscosity for easy stirring. Typical diluents are lubricating oil and liquid compounds containing only carbon and hydrogen. If desired, ammonium hydroxide may also be added to the reaction mixture to provide a solution of ammonium molybdate. This reaction is carried out at a temperature from the melting point of the mixture to reflux temperature. It is ordinarily carried out at atmospheric pressure although higher or lower pressures may be used if desired. This reaction mixture is treated with a sulfur source as defined above at a suitable pressure and temperature for the sulfur source to react with the acidic molybdenum and basic nitrogen compounds. In some cases, removal of water from the reaction mixture may be desirable prior to completion of reaction with the sulfur source.

In the reaction mixture, the ratio of molybdenum compound to basic nitrogen compound is not critical; however, as the amount of molybdenum with respect to basic nitrogen increases, the filtration of the product becomes more difficult. Since the molybdenum component probably oligomerizes, it is advantageous to add as much molybdenum as can easily be maintained in the composition. Usually, the reaction mixture will have charged to it from 0.01 to 2.00 atoms of molybdenum per basic nitrogen atom. Preferably from 0.4 to 1.0, and most preferably from 0.4 to 0.7, atoms of molybdenum per atom of basic nitrogen is added to the reaction mixture.

The sulfur source is usually charged to the reaction mixture in such a ratio to provide 0.1 to 4.0 atoms of sulfur per atom of molybdenum. Preferably from 0.5 to 3.0 atoms of sulfur per atom of molybdenum is added, and most preferably, 1.0 to 2.6 atoms of sulfur per atom of molybdenum.

The polar promoter, which is preferably water, is ordinarily present in the ratio of 0.1 to 50 mols of promoter per mol of molybdenum. Preferably from 0.5 to 25 and most preferably 1.0 to 15 mols of the promoter is present per mol of molybdenum.

The lubricating oil compositions containing the additives of this invention can be prepared by admixing, by conventional techniques, the appropriate amount of the molybdenum-containing composition with a lubricating oil. The selection of the particular base oil depends on the contemplated application of the lubricant and the presence of other additives. Generally, the amount of the molybdenum containing additive will vary from 0.05 to 15% by weight and preferably from 0.2 to 10% by weight.

The lubricating oil which may be used in this invention includes a wide variety of hydrocarbon oils, such as naphthenic bases, paraffin bases and mixed base oils as well as synthetic oils such as esters and the like. The lubricating oils may be used individually or in combination and generally have a viscosity which ranges from 50 to 5,000 SUS and usually from 100 to 15,000 SUS at 38° C.

In many instances it may be advantageous to form concentrates of the molybdenum containing additive within a carrier liquid. These concentrates provide a convenient method of handling and transporting the additives before their subsequent dilution and use. The concentration of the molybdenum-containing additive within the concentrate may vary from 0.25 to 90% by weight although it is preferred to maintain a concentration between 1 and 50% by weight. The final application of the lubricating oil compositions of this invention may be in marine cylinder lubricants as in crosshead diesel engines, crankcase lubricants as in automobiles and railroads, lubricants for heavy machinery such as steel mills and the like, or as greases for bearings and the like. Whether the lubricant is fluid or a solid will ordinarily depend on whether a thickening agent is present. Typical thickening agents include polyurea acetates, lithium stearate and the like.

If desired, other additives may be included in the lubricating oil compositions of this invention. These additives include antioxidants or oxidation inhibitors, dispersants, rust inhibitors, anticorrosion agents and so forth. Also anti-foam agents stabilizers, anti-stain agents, tackiness agents, anti-chatter agents, dropping point improvers, anti-squawk agents, extreme pressure agents, odor control agents and the like may be included.

Certain molybdenum products that can be prepared by the process of invention also find utility in making brake lining materials, in high-temperature structural materials, in iron and steel alloys, in cladding materials, in electroplating solutions, as components for electrical discharge machine electrodes, as fuel additives, in making self-lubricating or wear-resistant structures, as mold release agents, in compositions for phosphatizing steel, in brazing fluxes, in nutrient media for microorganisms, in making electrosensitive recording material, in catalysts for refining coal, oil, shale, tar sands, and the like or as stabilizers or curing agents for natural rubber or polymers.

The following examples are presented to illustrate the operation of the invention and are not intended to be a limitation upon the scope of the claims.

EXAMPLE 1

To a 500 ml flask was added 290 grams of a solution of 45% concentrate in oil of the succinimide prepared from polyisobutenyl succinic anhydride and tetraethylene pentaamine and having a number average molecular weight for the polyisobutenyl group of about 980 and 150 ml hydrocarbon thinner. The mixture was heated to 120° C. Then over a period of 45 minutes at 100° to 110° C., there was added a solution containing 28.8 grams molybdenum trioxide dissolved from 12.9 grams of concentrated ammonium hydroxide diluted to 100 ml with water (0.21 mols of ammonia). The reaction mixture was heated to refluxing (approximately 155° C.) and held at this temperature for one hour. Hydrogen sulfide gas was added at 115° C. A total of 10 grams hydrogen sulfide was added and then the reaction mixture was flushed with nitrogen for one hour at 110° C. The mixture was then heated to 155° C. and held at this temperature for one hour. To the mixture was added 100 ml of hydrocarbon thinner and then the mixture was filtered hot through diatomaceous earth. The product was stripped to 160° C. at 20 mm Hg to yield 316.6 grams of product containing 4.94% molybdenum, 2.77% oxygen, 2.10% sulfur and 1.91% nitrogen.

EXAMPLE 2

A solution of 28.8 grams molybdenum trioxide dissolved in 0.2 mols ammonia from 12.9 ml of concentrated ammonium hydroxide diluted to 100 ml with water was added dropwise over a period of 45 minutes at 100° to 105° C. to a solution of 290 grams of the succinimide described in Example 1. The reaction mixture was heated to reflux at approximately 155° C. and held at this temperature for one hour. The mixture was then heated to 140° C. and 4 grams sulfur was added. The temperature was increased to reflux at 155° C. and held at reflux for one hour. The temperature was then increased to 165° to 170° C. and held for two hours. To the mixture was then added 100 ml of hot hydrocarbon thinner to give approximately 200 ml of solvent in the reaction flask. The mixture was filtered hot through diatomaceous earth and then stripped at 160° C. and 20 mm Hg to give 312.8 grams of product containing 5.39% molybdenum, 1.75% nitrogen, 3.50% oxygen and 1.30% sulfur.

EXAMPLE 3

To a 1 liter flask was added 290 grams of the succinimide described in Example 1 and 150 ml hydrocarbon thinner. The reaction mixture was heated to 65° C. and 28.8 grams of molybdenum trioxide and 50 ml of water was added. The temperature was maintained at 65° to 70° C. for ½ hour and then raised to 150° C. After 50 minutes and at 150° C., 5 grams of elemental sulfur and 50 ml of hydrocarbon thinner was added. The temperature was increased to 155° to 160° C. (reflux) over a period of ½ hour. Some solvent was removed and the temperature was increased to 165° to 170° C. The mixture was held at this temperature for two hours. To the mixture was added 50 ml of hydrocarbon thinner and the mixture was filtered through diatomaceous earth and then stripped to 160° C. at 20 mm Hg to yield 314.5 grams of product containing 4.93% molybdenum, 3.59, 3.48% oxygen, 1.92% nitrogen and 1.49% sulfur.

EXAMPLE 4

To a 1 liter flask containing 290 grams of the succinimide described in Example 1 and 150 ml hydrocarbon thinner. The mixture was heated to 65° C. and 28.8 grams molybdenum trioxide, and 50 ml water was added. The temperature was maintained at 65%° C. for ½ hour and increased to 150° C. over a period of 55 minutes. To the mixture was added 7 grams elemental sulfur and 100 ml of hydrocarbon thinner. The reaction mixture was maintained at reflux at approximately 155° C. for 45 minutes and then the temperature was increased to 165° to 170° C. and held there for two hours. To the mixture was added 50 ml of hydrocarbon thinner and the reaction mixture was filtered hot through diatomaceous earth. The filtrate was stripped to 160° C. at 20 mm Hg to yield 316.5 grams of product containing 6.35% molybdenum, 3.57% oxygen, 1.86% nitrogen, 2.15% sulfur.

EXAMPLE 5

To a 1 liter flask was added 290 grams of the succinimide described in Example 1 molybdenum trioxide, 50 ml water and 150 ml hydrocarbon thinner. The reaction mixture was heated to 65° C. and maintained at this temperature for ½ hour. Then 6 grams of hydrogen sulfide was added at 63°–65° C. over a period of 15 minutes. After addition, the temperature was maintained at 63°–65° C. for one hour with vigorous stirring and under nitrogen atmosphere. The temperature was then raised to 100° C. to remove most of the water and then to 155° to 160° C. and held at reflux for one hour. The mixture was filtered hot through diatomaceous earth and then stripped to 160° C. at 20 mm Hg to yield 314.15 grams of product containing 5.87% molybdenum, 3.64% oxygen, 2.05% nitrogen, 0.75% sulfur and 0.08% sediment.

EXAMPLE 6

To a 1-liter flask was added 290 grams of the succinimide described in Example 1 and 150 ml hydrocarbon thinner. The reaction mixture was heated to 65° C. and 28.8 grams molybdenum trioxide and 50 ml of water was added. The temperature was held at 65° C. for ½ hour and raised slowly to 155° C. at 120° C., 10 grams of elemental sulfur was added and the reaction mixture was then held at 155° C. for 30 minutes, 160° C. for 15 minutes, 170° C. for 30 minutes, 175° C. for 30 minutes and 180° C. for 30 minutes. Then 120 ml of hydrocarbon thinner was added and the reaction mixture was filtered through diatomaceous earth and the filtrate stripped to 160° C. at 20 mm Hg to yield a product containing 5.70% molybdenum, 2.88% oxygen, 1.83% nitrogen, and 2.94% sulfur.

EXAMPLE 7

To a 3-liter flask was added 1160 grams of succinimide described in Example 1 and 800 ml of hydrocarbon thinner. The reaction mixture was heated to 65° C. and 200 ml water and 116 grams $MoO_3$ was added. The temperature was increased to reflux (98° C.) and held at this temperature for 2½ hours until the solution became clear green. Water was removed at up to a temperature of 140° C. (bottoms). Then 60 grams of sulfur was added. The temperature was increased to 155° C. over a period of 15 minutes and held at this temperature for ½ hour. The temperature was then increased to 180° C. over a period of 30 minutes and held at this temperature for 3½ hours. The mixture was then cooled and left overnight. Then 200 ml hydrocarbon thinner solvent was added and the solution heated to 130° C. It was then filtered through diatomaceous earth and stripped to 200° C. at 20 mm Hg to yield 1287 grams of product containing 4.49% sulfur, 5.82% molybdenum and 2.58% oxygen.

EXAMPLE 8

To a 3-liter flask was added 1160 grams of a polyamide prepared from a $C_{18}$ carboxylic acid and tetraethylenepentaamine and containing 6.29% nitrogen and 800 ml hydrocarbon thinner. The mixture was heated to 65° C. and 200 ml of water and 116 grams $MoO_3$ was added. The temperature was raised to reflux, approximately 95° C., and held at this temperature for 4 hours until the solution became clear green. The solvent was removed to 150° C. maximum and the mixture was then cooled to 140° C. and 28 grams sulfur was added. The temperature was raised to 155° C. over a period of ¼ hour and held at this temperature for ½ hour. The temperature was again increased to 175° C. over a period of 20 minutes and the held at between 175° and 180° C. for 2 hours. the mixture was cooled and left overnight and then 200 ml hydrocarbon solvent was added. The mixture was heated to 130° C., filtered through diatomaceous earth and then stripped to 180° C. bottoms at 20 mm Hg to yield 1282 grams of product containing 5.45% nitrogen, 2.15% sulfur, 5.51% molybdenum, and 5.73% oxygen.

EXAMPLE 9

To a 1-liter flask was added 400 grams of the reaction product of polyisobutenylchloride wherein the polyisobutene group has a number average molecular weight of 1,400 and ethylene diamine in a hydrocarbon solvent. The mixture was stripped to 160° C. bottoms at 20 mm Hg and cooled to yield 289 grams of product containing 1.58% nitrogen. To this was added 200 ml of hydrocarbon thinner, 50 ml water and 29b grams of $MoO_3$. The mixture was stirred at reflux, approximately 101° C. for 2 hours, and then stripped to 140° C. bottoms. Then 7 grams of sulfur was added and the temperature was increased to 155° C. over a period of 10 minutes and held at this temperature for ½ hour. The temperature was then raised to 180° C. over a period of 10 minutes and held at 180° to 185° C. for 2 hours. The mixture was cooled and 100 ml hydrocarbon thinner was added. The mixture was then filtered through diatomaceous earth and after an addition of 100 grams of neutral lubricating oil was stripped to 180° C. bottoms at 20 mm Hg to yield 409 grams of product.

EXAMPLE 10

To a 1-liter flask was added 290 grams of a Mannich base prepared from dodecylphenol, methylamine and formaldehyde and having an alkalinity value of 110 and containing 2.7% nitrogen, and 200 ml of a hydrocarbon thinner. The mixture was heated to 65° C. and 50 ml water and 29 grams of molybdenum trioxide was added. The mixture was stirred at reflux, 104° to 110° C., for 4½ hours. The solution became a clear dark brown color and then was stripped to 175° C. bottoms. The mixture was cooled to 140° C. and 7 grams sulfur was added. The temperature was increased to 155° C. over a period of 7 minutes and held at this temperature for ½ hour. The temperature was then increased to 180° C. over a period of 10 minutes and held for 2 hours. The mixture was then cooled and left overnight. The next day 100 ml of hydrocarbon solvent was added. The mixture was heated to 100° C. and filtered through diatomaceous earth and then stripped to 180° C. at 20 mm Hg to yield 317 grams of product.

EXAMPLE 11

To a 3-liter flask was added 1160 grams of succinimide as described in Example 1 and 800 ml of hydrocarbon thinner. This mixture was heated to 65° C. and 200 ml water and 116 grams of $MoO_3$ was added. The mixture was stirred at reflux (96° C.) for 2 hours. It was cooled and an additional 116 grams of $MoO_3$ was added. This mixture was stirred at reflux (97° C.) for 10 hours. The mixture was cooled and allowed to stand overnight. It was then stripped to 180° C., cooled to 140° and 60 grams of sulfur was added. The temperature was then increased to 155° C. over a period of 15 minutes and held at this temperature for ½ hour and then heated to 180° C. over a period of 15 minute and held at this temperature for 3 hours. The mixture was cooled and 200 ml hydrocarbon thinner was added. Then the solution was heated to 130° C. and filtered through diatomaceous earth with addition of hydrocarbon thinner to aid in filtration. The filtrate was stripped to 200° C. and 20 mm Hg to yield 1325 grams of product.

EXAMPLE 12 (B-3721-49)

To a 1 liter flask was added 400 g of the hydrocarbyl polyamine described in Example 9 which was stripped to 160° C. at 20 mm Hg and then 200 ml hydrocarbon thinner, 50 ml water and 29 g $MoO_3$ was added. The mixture was stirred at 101° C. for 2 hours and then heated to 140° C. to remove water. Sulfur (7 g) was added and the temperature was gradually increased to 180°–185° C. where it was held for 2 hours. After cooling, 100 ml hydrocarbon thinner was added and the mixture was filtered through diatomaceous earth and stripped at 180° C. and 20 mm Hg to yield 409 g of product containing Mo 4.67% (neutron activation), 4.93 (x-ray fluorescense); O, 1.37%; S, 1.94%.

EXAMPLE 13

To a 1 liter flask containing at 65° C. 289 g of the stripped polyamine described in Example 12 and 200 ml hydrocarbon thinner was added 50 ml water and 29 g $MoO_3$. The mixture was stirred at reflux for 2 hours and then stripped at 175° C. After cooling to 110°–115° C., 10 g of $H_2S$ was added. Then the mixture was heated to 155°–160° C. and held for 1 hour. After cooling, 75 ml hydrocarbon thinner was added and the mixture was filtered through diatomaceous earth. Neutral oil (100 g) was added and the mixture was stripped to 180° C. at 20 mm Hg to yield 412 g of product containing N, 0.90%; S, 2.31%; Mo, 4.21 (N.A.), 4.67 (XRF); O, 1.01.

EXAMPLE 14

To a 1 liter flask containing 300 g of a borated Mannich base prepared from a $C_{80-100}$ alkylphenol, formaldehyde and tetraethylene pentaamine or triethylene tetraamine, or mixtures thereof and containing urea (Amoco 9250) and 200 ml hydrocarbon thinner at 65° C. was added 40 ml water and 25 g $MoO_3$. The mixture was stirred at reflux for 4.5 hours and then stripped to 165° C. After cooling to 140° C., 7 g sulfur was added and the temperature was gradually increased to 185° C. where it was held for 2 hours. Then, 75 ml hydrocarbon thinner was added and the mixture was filtered through diatomaceous earth and then stripped to 180° C. at 20 mm Hg to yield 307 g product containing N, 1.04%; S, 2.53%; Mo, 4.68% (N.A.), 4.99% (XRF); O, 2.53%, B, 0.22%.

EXAMPLE 15

To a 3 liter flask was added 500 g of a concentrate of polyisobutenyl succinic anhydride wherein the polyisobutenyl group had a number average molecular weight of about 980 and 36 g dimethyl aminopropylamine. The temperature of the reaction mixture was increased to 160° C., held there for 1 hour and then stripped to 170° C. at 20 mm Hg. To this mixture was added 350 ml hydrocarbon thinner, 50 ml water, and 29 g $MoO_3$. This mixture was stirred at reflux for 2 hours and then stripped to 140° C. to remove water. Then 7 g of sulfur was added and the mixture was held at 180°–185° C. for 2 hours. After cooling, additional hydrocarbon thinner was added and the mixture was filtered through diatomaceous earth, and then stripped to 180° C. at 20 mm Hg to yield 336 g product containing N, 1.17%; S, 1.55%; Mo, 3.37% (N.A.), 3.31% (XRF); O, 2.53%.

EXAMPLE 16

To a 1 liter flask containing 290 g of the succinimide described in Example 1 and 200 ml of hydrocarbon thinner at 65° C. was added 50 ml water and 29 g $MoO_3$. The mixture was stirred at reflux for 1.5 hours and then stripped to 165° C. to remove water. After cooling to 100° C., 40 g butyldisulfide was added and the mixture was heated to 180°–185° C. for 2.5 hours. Then an additional 100 ml hydrocarbon thinner was added before filtering through diatomaceous earth and stripping to 180° C. at 20 mm Hg to yield 305 g of product containing N, 1.90%; S, 0.47%; Mo, 6.21% (N.A.), 6.34% (XRF); O, 4.19 (N.A.).

EXAMPLE 17

To a 1 liter flask containing 290 g of the succinimide described in Example 1 and 200 ml hydrocarbon thinner at 75° C. was added 50 ml water and 29 g $MoO_3$. The mixture was refluxed for 1.5 hours and then stripped to 200° C. to remove water. After cooling to 100° C., 19 g thioacetamide was added and the mixture was gradually heated to 200° C. where it was held for 0.75 hours. Then, 150 ml hydrocarbon thinner was added and the mixture was filtered through diatomaceous earth and stripped to 180° C. at 20 mm Hg, to yield a product containing N, 1.46%; S, 2.05%; Mo, 4.57% (N.A.), 4.70% (XRF); O, 2.38%. Before testing, this product was diluted with 100 g netural lubricating oil.

EXAMPLE 18

To 292 g of the starting material described in Example 13 was added 200 ml hydrocarbon thinner, 50 ml water, and 33.5 g ammonium paramolybdate. The mixture was refluxed for 21 hours and then stripped to remove water. After cooling to 140° C., 7 g sulfur was added. The mixture was heated to 180°–185° C. and held for 2 hours. After addition of 100 ml hydrocarbon thinner, the mixture was filtered through diatomaceous earth. Neutral diluent oil (100 g) was added and the mixture was stripped to 180° C. at 20 mm Hg to yield 414 g product containing N, 0.92%; S, 2.02%; Mo, 4.57% (N.A.), 4.60% (XRF); O, 1.37%.

EXAMPLE 19

To a 3 liter flask containing 1160 g of the succinimide described in Example 1 and 800 ml hydrocarbon thinner at 75° C. was added 200 ml water and 116 g $MoO_3$. The mixture was refluxed for 3 hours and then stripped to 180° C. to remove water. At 110° C., about 64 g $H_2S$ was added. Additional hydrocarbon thinner (200 ml) was added and the mixture was filtered through diatomaceous earth and then stripped to 180° C. at 20 mm Hg to yield 1290 g of product containing N, 1.85%; S, 4.24%; Mo, 5.92 (N.A.), 5.83% (XRF), O, 2.12%.

EXAMPLE 20

To a 1 liter flask containing 1160 g of the succinimide described in Example 1 and 800 ml hydrocarbon thinner at 75° C. was added 200 ml water and 116 g $MoO_3$. The mixture was stirred at reflux for 3 hours and then heated to 186° C. to remove water. After cooling to 110° C., 35 g $H_2S$ was added. The mixture was heated to 182° C., then 200 ml hydrocarbon thinner was added and the mixture was filtered through diatomaceous earth. Stripping to 180° C. at 20 mm Hg yielded 1272 g of product containing N, 1.93%; S, 3.20%; Mo, 5.90% (N.A.); O, 3.01%.

EXAMPLE 21

To a 1 liter flask containing 290 g of the succinimide described in Example 1 and 200 ml hydrocarbon thinner at 75° C. was added 50 ml water and 29 g MoO₃. The mixture was stirred at reflux for 1.5 hours and then heated to 187° C. to remove water. Then 100 ml hydrocarbon thinner was added and, at 75° C., 34 g of aqueous ammonium polysulfide (31% free sulfur). This mixture was slowly heated to 180° C. and held there for 2.25 hours. It was then filtered through diatomaceous earth and stripped to 180° C. at 20 mm Hg to yield 318 g of product containing N, 1.89%; S, 4.07%; Mo, 6.16% (N.A.).

EXAMPLE 22

To a 1 liter flask containing 290 g of the succinimide described in Example 1 and 200 ml hydrocarbon thinner at 75° C. was added 50 ml water and 29 g MoO₃. This mixture was refluxed for 3 hours and then heated to 195° C. to remove water. After cooling to 70° C., 58 g of a 52-60% technical solution of ammonium sulfide was added. The reaction mixture was heated to 180°-185° C. for 4 hours. After cooling to 115° C., 125 ml hydrocarbon thinner was added, the mixture was filtered through diatomaceous earth, and then stripped to 180° C. at 25 mm Hg to yield 318 g of product containing 6.19% Mo (XRF).

EXAMPLE 23

To a 1 liter flask containing 330 g of a concentrate containing 1.50% N in oil of a polyisobutenyl succinimide prepared from triethylenetetraamine and a polyisobutenyl succinic anhydride wherein the polyisobutenyl group has a number average molecular weight of 980, and 200 ml hydrocarbon thinner at 75° C. was added 50 ml water and 22 g MoO₃. This mixture was stirred at reflux (about 100° C.) for 11 hours. It was then heated to 180° C. to remove water. After cooling to 140° C., 9 g sulfur was added and the mixture was slowly heated to 180° C. where it was held for 3 hours. After adding 100 ml hydrocarbon thinner, the mixture was filtered through diatomaceous earth and then stripped to 180° C. at 20 mm Hg to yield 347 g of product containing Mo, 4.13% (N.A.), 3.98% (XRF); N, 1.42%; S, 2.66%; O, 2.85% (N.A.).

EXAMPLE 24

To 291 g of the starting material used in Example 13 and 200 ml hydrocarbon thinner at 75° C. was added 50 ml water and 29 g MoO₃. The mixture was stirred at reflux for 3 hours and then heated to 180° C. to remove water. After cooling to 140° C., 15 g of sulfur was added and the mixture was gradually heated to 180°-185° C. where it was held for 2.5 hours. After adding 200 ml hydrocarbon thinner, the mixture was filtered through diatomaceous earth and then 100 g neutral diluent oil was added. Stripping to 200° C. at 20 mm Hg yielded 410 g of product containing Mo, 4.68% (N.A.).

EXAMPLE 25

To a 1 liter flask containing 47 g tetraethylene pentaamine was added 404 g polyisobutenyl succinic anhydride having a PIBSA number of 76.7. The mixture was heated to 150°-160° C. where it was held for 1.5 hours. It was then stripped to 160° C. at 20 mm Hg to yield 439 g of polyisobutenyl succinimide. To this succinimide was added 300 ml hydrocarbon solvent, 135 ml water, and 80 g MoO₃. The mixture was stirred at reflux for 6.5 hours and then heated to 180° C. to remove water. After cooling to 140° C., 41 g sulfur was added and the temperature gradually increased to 180°-185° C. where it was held for 4 hours. After addition of 200 ml hydrocarbon thinner, the mixture was filtered through diatomaceous earth and then stripped to 200° C. at 20 mm Hg and 300 g neutral oil was added to yield 810 g of product containing 6.23% Mo by XRF.

EXAMPLE 26

To a 1 liter flask containing 290 g of the succinimide described in Example 1 and 200 ml hydrocarbon thinner at 75° C. was added 50 ml water and 29 g MoO₃. The mixture was stirred at 96°-98° C. for 2½ hours and then stripped at 191° C. After cooling to 75° C., 43 ml 1-butanethiol was added and the mixture was refluxed for 14 hours. The mixture was then stripped to 180° C. at 20 mm Hg to yield 318 g product containing Mo, 6.17% (XRF); N, 1.97%; S, 1.05%.

EXAMPLE 27

Lubricating oil compositions containing the additives prepared according to this invention have been tested in a variety of tests. Reported below are results from certain of these tests which are described as follows.

In the Oxidator B test the stability of the oil is measured by the time required for the consumption of 1 liter of oxygen by 100 grams of the test oil at 340° F. In the actual test, 25 grams of oil is used and the results are corrected to 100-gram samples. The catalyst which is used at a rate of 1.38 cc per 100 cc oil contains a mixture of soluble salts providing 95 ppm copper, 80 ppm iron, 4.8 ppm manganese, 1100 ppm lead, and 49 ppm tin. The results of this test are reported as hours to consumption of 1 liter of oxygen and our measure of the oxidative stability of the oil.

The anti-corrosion properties of compositions can be tested by their performance in the CRC L-38 bearing corrosion test. In this test, separate strips of copper and lead are immersed in the test lubricant and the lubricant is heated for 20 hours at a temperature of 295° F. The copper strip is weighed and then washed with potassium cyanide solution to remove copper compound deposits. It is then re-weighed. The weight losses of the two strips are reported as a measure of the degree of corrosion caused by the oil.

The copper strip test is a measure of corrosivity toward non-ferrous metals and is described as ASTM Test Method D-130. Anti-wear properties are measured by the 4-ball wear and the 4-ball weld tests. The 4-ball wear test is described in ASTM D-2266 and is run at 54° C. for 30 minutes using steel balls and a 40 kg weight and the 4-ball weld test is a variation of ASTM D-2783 run at ambient temperature until weld point with weights decreased by 5 kg until the pass load is determined. The coefficient of friction of a lubricating oils containing additives of this invention was tested in the Kinetic Oiliness Testing Machine (KOTM) manufactured by G. M. Neely of Berkeley, California. The procedure used in this test is described by G. L. Neely, Proceeding of Mid-Year Meeting, American Petroleum Institute 1932, pages 60-74 and in ASLE Transactions, Vol. 8, pages 1-11 (1965) and ASLE Transactions, Vol. 7, pages 24-31 (1964). The coefficient of friction was measured under boundary conditions at 150° and 204° C. using a 1 Kg load and a molybdenum-filled ring on a cast-iron disk. The data for some of the tests run on compositions of this invention is reported in the Table below.

Unless otherwise noted, the formulation tested contained, in a neutral lubricating oil, 3.5% of a 50% concentrate of polyisobutenyl succinimide 20 mmoles/kg sulfurized calcium phenate, 30 mmoles/kg overbased magnesium sulfonate, 5.5% viscosity index improver, and 22 mmoles/kg product of this invention. (If necessary, additional succinimide was added to bring the total nitrogen content of the finished oil to 2.1%.)

TABLE

| Example | Oxidator B, hrs. | ASTM D-2266, mm | ASTM D-2783 D kg | L-38 Cu, mg | L-38 Pb, mg | D-130 | Coefficient of Friction 150° C. | Coefficient of Friction 204° C. |
|---|---|---|---|---|---|---|---|---|
| 1 | 9.6 | .42 | 160 | 21.2 | 0.5 | 2a | | |
| 2 | 13.1 | .43 | 165 | 21.9 | 1.0 | 1b | | |
| 3 | 11.8 | .49 | 160 | 18.3 | 5.3 | 2a | | |
| 4 | 11.0 | .52 | 170 | 19.9 | 1.2 | 2a | | |
| 5 | | | | | | | | |
| 6 | 10.4 | .37 | 155 | 15.0 | 0.4 | 1b | | |
| 7 | | | | | | | | |
| 8 | | | | | | | | |
| 9 | | | | | | | | |
| 10 | | | | | | | | |
| 11 | | | | | | | | |
| 12 | 9.5 | 0.43 | | | | 1a[1] | | |
| 13 | 7.8 | .51 | 165 | | | 1a[1] | .131 | .061 |
| 14 | 9.0 | | 155 | | | 1b[1] | .110 | .035 |
| 15 | 8.7 | .55 | 175 | | | 1b[1] | .115 | .045 |
| 16 | 8.0 | .53 | 145 | | | 1a[1] | .122 | .100 |
| 17 | 7.8 | | | | | 1a[1] | .120 | .081 |
| 18 | 7.9 | .46 | 155 | | | 1a[1] | .118 | .060 |
| 19 | 7.4 | .40 | 165 | | | 1b/2a[1] | .050 | .040 |
| 20 | 9.0 | .48 | 170 | | | 1a[1] | .075 | .039 |
| 21 | | | | | | 1b/2a[1] | | |
| 22 | | | | | | 1b[1] | | |
| 23 | | | | | | 1a[2] | | |
| 24 | | | | | | 1a/1b[3] | | |
| 25 | | | | | | 1b | | |
| 26 | | | | | | 1c[1] | | |

[1] Molybdenum compound tested at 4% wt. in neutral oil.
[2] Molybdenum compound tested at 6% wt. in neutral oil.
[3] Molybdenum compound tested at 5% wt. in neutral oil.

What is claimed is:

1. A process for preparing a molybdenum-containing composition which comprises (1) reacting an acidic molybdenum compound and a basic nitrogen compound selected from the group consisting of a succinimide, carboxylic acid amide, Mannich base, phosphonamide, thiophosphonamide, phosphoramide, dispersant viscosity index improvers, or mixtures thereof, in the presence of a polar promoter, to form a molybdenum complex wherein from 0.01 to 2 atoms of molybdenum are present per basic nitrogen atom, and the promoter is present in the ratio of 0.01 to 50 moles of said polar promoter per mole of molybdenum; and (2) reacting said complex with a sulfur containing compound, in an amount to provide 0.1 to 4.0 atoms of sulfur per atom of molybdenum, to form a sulfur- and molybdenum-containing composition.

2. The process of claim 1 wherein the sulfur source is sulfur, hydrogen sulfide, phosphorus pentasulfide, $R_2S_x$ where R is hydrocarbyl, and x is at least 2, inorganic sulfides or inorganic polysulfides, thioacetamide, thiourea, mercaptans of the formula RSH where R is hydrocarbyl, or a sulfur-containing antioxidant.

3. The process of claim 2 wherein the sulfur source is sulfur, hydrogen sulfide, phosphorus pentasulfide, $R_2S_x$ where R is $C_{1-4}$ hydrocarbyl, and x is at least 3, inorganic sulfides, or inorganic polysulfides, thioacetamide, thiourea or RSH where R is $C_{1-40}$ alkyl, and the acidic molybdenum compound is molybdic acid, ammonium molybdate, or alkali metal molybdates.

4. The process of claim 3 wherein said sulfur source is sulfur, hydrogen sulfide, RSH where R is $C_{1-10}$ alkyl, phosphorus pentasulfide, or $(NH_4)_2S_{x'}$, where x' is at least 1, said acidic molybdenum compound is molybdic acid, or ammonium molybdate, and said basic nitrogen compound is a succinimide, carboxylic acid amide, or Mannich base.

5. The process of claim 4 wherein said basic nitrogen compound is a $C_{24-350}$ hydrocarbyl succinimide, carboxylic acid amide, or a Mannich base prepared from a $C_{9-200}$ alkylphenol, formaldehyde, and an amine.

6. The process of claim 5 wherein said basic nitrogen compound is a polyisobutenyl succinimide prepared from polyisobutenyl succinic anhydride and tetraethylene pentaamine or triethylene tetraamine.

7. The process of claim 5 wherein said basic nitrogen compound is a carboxylic acid amide prepared from one or more carboxylic acids of the formula $R^2COOH$, or a derivative thereof which upon reaction with an amine yields a carboxylic acid amide, wherein $R^2$ is $C_{12-350}$ alkyl or $C_{12-350}$ alkenyl and a hydrocarbyl polyamine.

8. The process of claim 7 wherein $R^2$ is $C_{12-20}$ alkyl or $C_{12-20}$ alkenyl and the hydrocarbyl polyamine is tetraethylene pentaamine or triethylene tetraamine.

9. The process of claim 5 wherein said basic nitrogen compound is a Mannich base prepared from dodecylphenol, formaldehyde, and methylamine.

10. The process of claim 5 wherein said basic nitrogen compound is a Mannich base prepared from $C_{80-100}$ alkylphenol, formaldehyde and triethylene tetraamine, tetraethylene pentaamine, or mixtures thereof.

11. The process of claim 1, 2, 3, 4, 5, 6, 7, 8, 9, or 10 wherein said polar promoter is water.

12. The product prepared by the process of claim 1, 2, 3, 4, 5, 6, 7, 8, 9, or 10.

13. The product prepared by the process of claim 11.

14. A lubricating oil composition comprising an oil of lubricating viscosity and from 0.05 to 15% by weight of the product of claim 12.

15. A lubricating oil composition comprising an oil of lubricating viscosity and from 0.05 to 15% by weight of the product of claim 13.

16. A lubricating oil concentrate composition comprising an oil of lubricating viscosity and from 15 to 90% by weight of the product of claim 12.

17. A lubricating oil concentrate composition comprising an oil of lubricating viscosity and from 15 to 90% by weight of the product of claim 13.

* * * * *